United States Patent
Sun et al.

(10) Patent No.: US 9,856,454 B2
(45) Date of Patent: Jan. 2, 2018

(54) RAPID MINCING OF ADIPOSE TISSUES TO ISOLATE LIVE CELLS IN VITRO

(71) Applicant: HUALIEN TZU CHI HOSPITAL, BUDDHIST TZU CHI MEDICAL FOUNDATION, Hualien (TW)

(72) Inventors: Li-Yi Sun, Hualien County (TW); Dian-Kun Li, Hualien County (TW); Cheng-Yoong Pang, Hualien County (TW); Yao-Jen Chang, Hualien County (TW)

(73) Assignee: Hualien Tzu Chi Hospital, Buddhist Tzu Chi Medical Foundation, Hualien (TW)

( * ) Notice: Subject to any disclaimer, the term of this patent is extended or adjusted under 35 U.S.C. 154(b) by 0 days.

(21) Appl. No.: 14/191,675

(22) Filed: Feb. 27, 2014

(65) Prior Publication Data

US 2015/0240210 A1 Aug. 27, 2015

(51) Int. Cl.
*C12N 5/0775* (2010.01)
*A61K 35/35* (2015.01)

(52) U.S. Cl.
CPC ............ *C12N 5/0667* (2013.01); *A61K 35/35* (2013.01)

(58) Field of Classification Search
CPC .............................. C12N 5/0667; A61K 35/35
See application file for complete search history.

(56) References Cited

U.S. PATENT DOCUMENTS

2011/0212064 A1    9/2011   Jansen et al.

FOREIGN PATENT DOCUMENTS

| CN | 1961069 A   | 5/2007  |
| CN | 102719396 A | 10/2012 |
| TW | 201235471 A | 9/2012  |
| TW | 201331366 A | 8/2013  |

OTHER PUBLICATIONS

De Ugarte et al., "Differential expression of stem cell mobilization-associated molecules on multi-lineage cells from adipose tissue and bone marrow." (2003) Immunology Letters, vol. 89: 267-270.*

Arana et al. "Adipose Tissue-Derived Mesenchymal Stem Cells: Isolation, Expansion, and Characterization" (2013) Methods in Molecular Biology, vol. 1036: 47-61.*
Ullah et al. "A Reliable Protocol for Isolation of Viable, Chondrogenically Differentiated Human Mesenchymal Stem cells from High-Density Pellet Cultures" (2012) BioResearch Open Access, vol. 1, No. 6: 297-305.*
Vellasamy et al. "Isolation and characterisation of mesenchymal stem cells derived from human placenta tissue." (2012) World Journal of Stem Cells, vol. 4, No. 6: 53-61.*
Gimble, "Adipose tissue-derived therapeutics" (2003) Expert Opinion on Biological Therapy, vol. 3, issue 5: 705-713.*
Burden, Guide to the Disruption of Biological Samples—2012 (2012) Random Primers, No. 12:1-25.*
IKA Manual "Technical Information of DT-20 Tube" IKA, available at http://www.ika.com/ika/product_art/manual/ika_ut_tube_drive_tubs.pdf, last accessed May 30, 2017.*
Kuan Lai et al., Allogeneic adipose-derived stem cells suppress Th17 lymphocytes in patients with active lupus in vitro. Acta Biochim Biophys Sin (Shanghai). Oct. 2011; 43(10):805-12.
Ultra-Turrax Tube Drive System. <seneco.it/prospetti/dispersori/tube%20drive%20prospetto.pdf> (2011) 7 pages.
Li-Yi Sun et al., Antioxidants cause rapid expansion of human adipose-derived mesenchymal stem cells via CDK and CDK inhibitor regulation. J Biomed Sci. 2013; 20(1): 53., Published online Aug. 1, 2013 (11 pages).
Office Action for Taiwan Application No. 102134332, dated Aug. 25, 2016 (22 pages).
Office Action for Chinese Application No. 201310478269.6, dated Dec. 21, 2016 (5 pages).
TW201331366 English abstract.
TW201235471 English abstract.
CN102719396 English abstract.
CN1961069 English abstract.

\* cited by examiner

Primary Examiner — Robert Yamasaki
Assistant Examiner — Teresa E Knight
(74) Attorney, Agent, or Firm — McCarter & English, LLP; Yu Lu (57) ABSTRACT

A method for rapid mincing of adipose tissues to isolate live cells in vitro is disclosed to overcome the drawbacks of a lead procedure of isolating live cells by holding a knife to mince adipose tissues, which can only isolate a small number of live cells and obtain low cell viability. The method includes: providing an adipose tissue; mincing the adipose tissue homogeneously by a mincing device; adding a reagent into the minced adipose tissue to perform hydrolysis; performing centrifuge and isolation; and removing a supernatant to obtain a cell pellet. Therefore, the time of mincing adipose tissues can be shortened, and contaminations caused by repeated use of the knife can be avoided. The method can be used for isolating live cells of adipose tissues to improve the number of live cells per unit weight of adipose tissues without reducing the cell viability.

24 Claims, 9 Drawing Sheets

RAPID MINCING OF ADIPOSE TISSUES TO ISOLATE LIVE CELLS IN VITRO

FIELD OF THE INVENTION

The present invention relates to a method for rapid mincing of adipose tissues to isolate live cells in vitro, and in particular, to a method using a cutting device to rapidly and homogeneously mincing adipose tissues, so as to facilitate isolating live cells from the adipose tissues to increase the live cells obtained from the adipose tissues of per unit weight and not reduce survival rate of the cells.

BACKGROUND OF RELATED ART

Due to mesenchymal stem cells can be separated from many different tissues of a human body; for example, an adipose tissue obtained by direct surgery excision or liposuction is just a rich source for a stem cell, which may separate ADSCs (Adipose Tissue-derived Stem Cells) that have the advantages of being low invasive in gaining method, having low harm to the human body, and being able to be proliferated and cultured in vitro.

At present, there is no such a set of suitable automatic system that can be matched with a treatment mode of mincing a lump adipose tissue obtained by direct surgery excision. A general treatment mode of mincing includes a patent of Republic of China with a patent No. 201331366 [serum-free culture expansion of somatic stem/progenitor cells in vitro], wherein a method thereof discloses that an adipose tissue lump is obtained by surgery, the adipose tissue is further minced by using surgical scissors, acts with a collagenase enzyme, and then is separated, thus obtaining a stromal vascular fraction (SVF) cell which can be together formed by a stroma cell, a blood cell, a vascular endothelial cell, an adipose-derived stem cell, etc. However, a longer time is taken to mince the adipose tissues as far as possible in the step of mincing the adipose tissue by using the surgical scissors in the method so as to obtain more SVF cells; while the longer the time spends on the mincing step, the higher the influences on the survival rate of the SVF cells are, such that the survival rate of the obtained ADSCs is relatively lower. In addition, it is easier for operating personnel to produce a risk of specimen cross-contamination when operating specimens from different sources due to repeatedly using the surgical scissors.

Like another patent of Republic of China with a patent No. 201235471 [Cell population Comprising Orbital Fat-derived Stem Cells (OFSCs) as well as isolation and Application Thereof], a method of the patent discloses that an orbital fat can be obtained via collecting from an orbital tissue directly removed from an inner orbital cavity, or obtained via collecting from an eyelid shaping surgery of eyelid entropion, eyelid eversion, eyelid ptosis or eye haustra; an orbital fat tissue can be simply dissected via a pair of scissors or tweezers, acts with a collagenase enzyme, and then is filtered and centrifugally separated so as to obtain a cell pellet; moreover, cell culture is implemented on the cell pellet so as to form a cell possessing a colony formation capacity. However, a longer time is also taken by the method disclosed in the case to mince the fat tissue as far as possible in the step of dissecting the orbital fat tissue by using the scissors or tweezers so as to obtain more cell pellets; and correspondingly, the longer the time spends on the mincing step, the higher the influences on the survival rate of the cells in the cell pellets are.

In conclusion, a method for rapid mincing of adipose tissues to isolate live cells is urgently needed for solving the defects of implementing adipose tissue mincing operation by using the surgical scissors in the prior art, so as to further increase live cells obtained from the adipose tissues of per unit weight under a condition of not reducing the survival rate of the cells.

SUMMARY OF THE INVENTION

At present, the inventor makes a study in view of the defects of the present method for separating the live cells in the adipose tissues, and provides a method for rapid mincing of adipose tissues to isolate live cells in vitro, so as to achieve the objectives of increasing the live cells obtained from the adipose tissues of per unit weight and not reducing the survival rate of the cells.

Therefore, the present invention provides a method for rapid mincing of adipose tissues to isolate live cells in vitro, comprising the steps as follows:

step (a) providing an adipose tissue; step (b) arranging the adipose tissue into an enclosed vessel of a cutting device; step (c) applying an acting force on the enclosed vessel by the cutting device to enable a preset cutting tool in the enclosed vessel to implement rapid and homogeneous mincing on the adipose tissue, thereby obtaining a homogenized adipose tissue; step (d) adding a reagent into the minced homogenized adipose tissue to implement a hydrolysis reaction; step (e) implementing filtering and centrifugal separation on the homogenized adipose tissue treated via the hydrolysis reaction; and step (f) removing a supernate after the centrifugal separation so as to obtain a cell pellet.

Further, a step of cleaning the adipose tissue via a phosphate buffer solution (PBS) may be included before step (a).

Further, the adipose tissue in step (a) is a lump adipose tissue obtained from surgery excision of a mammal.

Further, the mammal is a human being.

Further, the cutting device in step (b) is a disposable homogenizer of the cutting device.

Further, the disposable homogenizer comprises a disposable enclosed vessel and a power unit; moreover, the inside of the disposable enclosed vessel is provided with a cutting tool.

Further, a condition for homogeneous mincing in step (c) is to arrange 1 g to 6 g of adipose tissues into the disposable enclosed vessel with a volume of 15 ml to implement rapid and homogeneous mincing.

Further, a preferred condition for homogeneous mincing in step (c) is to arrange 3 g of adipose tissues into the disposable enclosed vessel with a volume of 15 ml to implement rapid and homogeneous mincing.

Further, a revolution of the power unit is 300-3000 rpm, and acting time of the power unit is 3-10 minutes.

Further, a preferred revolution of the power unit is 600-1500 rpm, and an optional revolution is 1200 rpm.

Further, the reagent in step (d) is selected from one of the groups or combinations thereof formed by a trypsin, a dispase, a gelatase, a hyaluronidase, a collagenase type I or a collagenase type IV.

Further, the method employs the collagenase type I or the collagenase type IV as an embodiment, wherein a working concentration is 0.2 mg/ml to 20 mg/ml.

Further, the hydrolysis reaction in step (d) is implemented in a constant temperature hybridization reaction oven for the whole process under conditions of 4-45 DEG C, 5 rpm-50 rpm and 0.5 h-24 h.

Further, the hydrolysis reaction step (d) is implemented in a constant temperature hybridization reaction oven for the whole process under conditions of 37 DEG C, 15 rpm and 8 h.

Further, the conditions for centrifugation in step (e) are 400×g and 10 minutes.

Further, step (e) comprises a step of moving a filtered fluid obtained after filtering slag of the adipose tissue into a centrifugal tube, so as to implement centrifugal separation.

Further, wherein the cell pellet in step (f) is a stromal vascular fraction (SVF) cell.

Further, a step (g) of adding the phosphate buffer solution into the cell pellet, cleaning the cell pellet, and then centrifuging again so as to remove a supernate comprising blood and the reagent to obtain a cell pellet after being cleaned is further included after step (f).

Further, a step (h) of arranging the cell pellet after being cleaned into a culture medium for culturing so as to obtain an amplified cell is further included after step (g).

Further, the amplified cell is an adipose tissue-derived stem cell which is undifferentiated substantially.

Further, the adipose tissue-derived stem cell at least shows a cell surface antigen CD90 or CD105, or a combination thereof, and does not show CD45.

Further, the culture medium comprises a basal culture medium (Iscove's modified Dulbecco's medium, IMDM), a serum additive and a basic fibroblast growth factor-2 (FGF-2).

Further, the serum additive is a fetal bovine serum with a volume percentage concentration of 2% to 10%, while a working concentration of the FGF-2 is 1 ng/ml to 20 ng/ml.

Further, a step (i) of implementing cryopreservation on the amplified adipose tissue-derived stem cell for further applications is included after step (h).

Further, step (i') of implementing induced differentiation on the amplified adipose tissue-derived stem cell so as to obtain a cell differentiated from the amplified adipose tissue-derived stem cell is included after step (h).

Further, the cell differentiated from the amplified adipose tissue-derived stem cell includes one of an osteogenic cell, an adipose cell or a cartilage cell.

The present invention provides a cell bank, comprising the amplified adipose tissue-derived stem cell receiving cryopreservation in step (i).

The present invention provides a medicine composition, comprising one or a combination of the cell differentiated from the adipose tissue-derived stem cell in step (i') or the adipose tissue-derived stem cell which is undifferentiated substantially obtained.

The present invention has the advantages as follows:

(I) Shortening a time spent on the step of mincing the adipose tissue: the present invention can shorten the time spent on the step of mincing the adipose tissue by using the cutting device than that of the method of the prior art that uses the surgical scissors to mince, and can reduce influences of the operating personnel caused by skill performance differences, thereby reducing a cell death phenomenon caused by that the cells in the adipose tissue live a human body for quite a long time, thus increasing the survival rate of the cells.

(II) Increasing yield of live cells: the present invention can homogeneously mince the adipose tissue by using the cutting device, so as to increase a contact area between the adipose tissue and a hydrolysis reaction reagent added and improve the hydrolysis reaction effects, so as to increase the stromal vascular fraction (SVF) cells obtained from the adipose tissues of per unit weight, increase the adipose tissue-derived stem cells (ADSCs), and do not reduce the survival rate of the cells.

(III) Reducing specimen cross-contamination: the present invention uses a disposable enclosed vessel and a power unit to implement rapid and homogeneous mincing step on the lump adipose tissue obtained, wherein specimens from different sources are respectively arranged in one disposable enclosed vessel, thus avoiding the cross-contamination phenomenon caused by error touch of the operating personnel when operating the specimens from different sources.

(IV) Obtaining the ADSCs possessing differentiation potentials: the ADSCs obtained via the method of the present invention at least show a cell surface antigen CD90 or CD105, or a combination thereof, and do not show CD45; moreover, the ADSCs have the capacities of being differentiated into bone, cartilage and fat, so that the ADSCs obtained via the method of the present invention become a rich source for pluripotent stem cells possessing differentiation potentials.

DETAILED DESCRIPTION OF THE PREFERRED EMBODIMENTS

To make the above and other objectives, characteristics and advantages of the present invention clearer and easier to understand, the following descriptions are described by reference to the FIGs and preferred embodiments.

Figure 1:
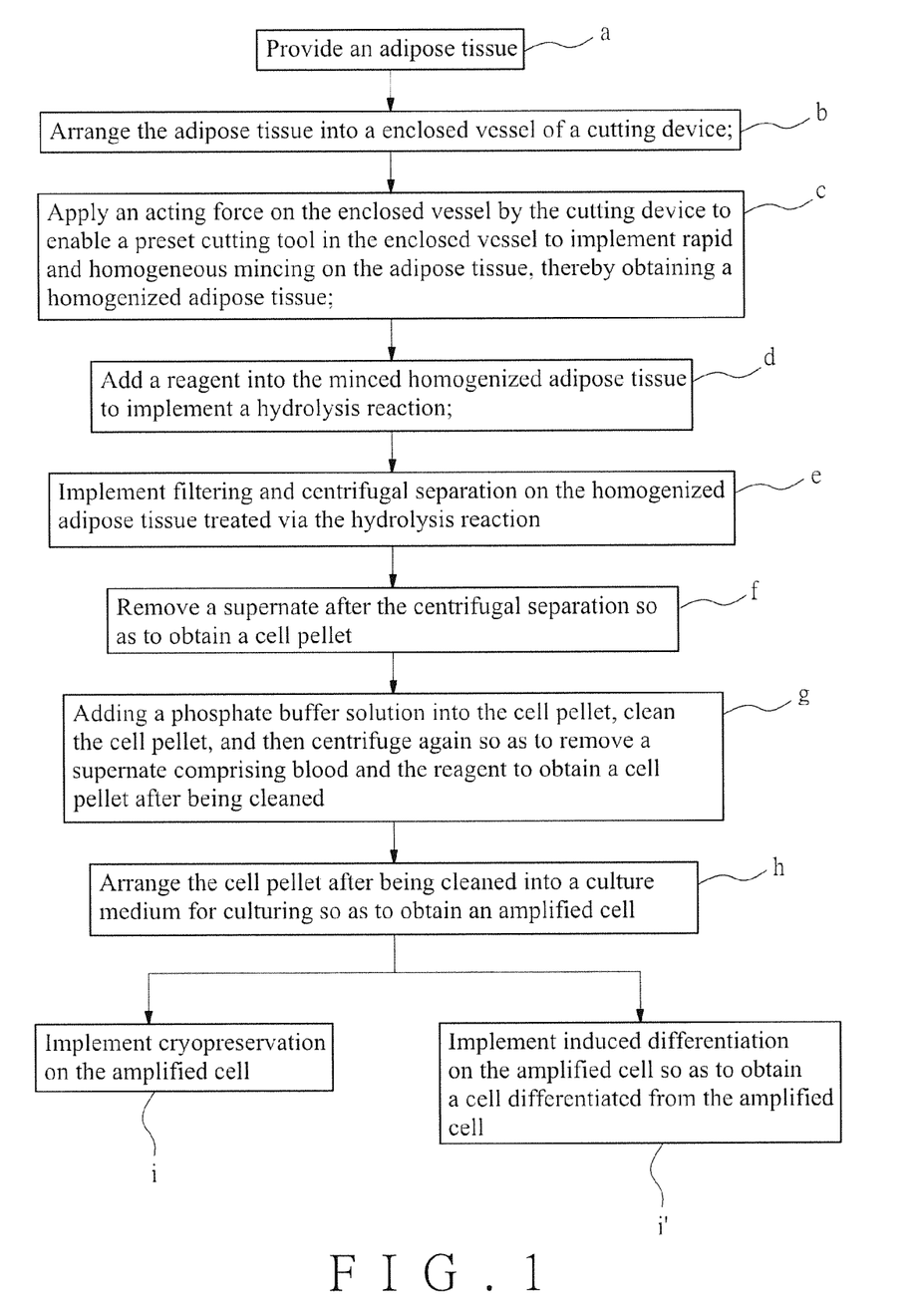
FIG. 1 is a flow chart of a method according to the present invention.
Figure 8:
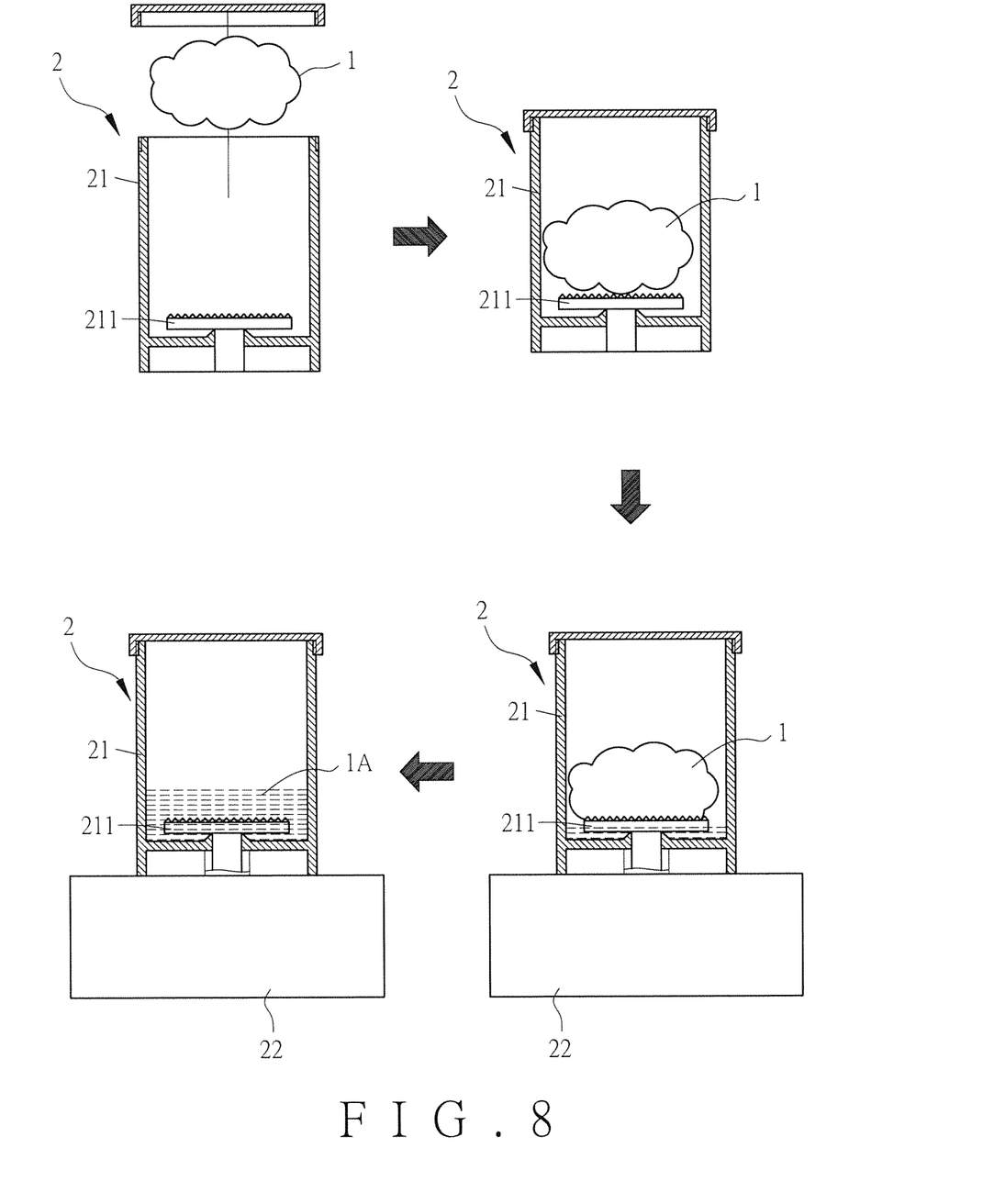
FIG. 8 is a schematic diagram for operation of step (b) and step (c) in the present invention.

Firstly, FIG. 1 is a flow chart of a method according to the present invention. The present invention provides a method for rapid mincing of adipose tissues to isolate live cells in vitro, comprising the steps as follows: in step (a), an adipose tissue which is a lump adipose tissue obtained from surgery excision of a mammal is provided, wherein the lump adipose tissue obtained from the surgery excision of a human beingis employed as an embodiment in the present invention; in step (b), the adipose tissue (1) is arranged into a disposable enclosed vessel (21) of a disposable homogenizer (2), wherein the disposable homogenizer (2) (DT-20 gamma, IKA ULTRA TURRAX Tube drive) comprises the enclosed vessel (21) with a volume of 15 ml and a power unit (22) and the inside of the disposable enclosed vessel (21) is provided with a cutting tool (211) (refer to FIG. 8); in step (c) an acting force is applied on the disposable enclosed vessel (21) by the power unit (22) to enable the cutting tool (211) in the disposable enclosed vessel (21) to implement rapid and homogeneous mincing on the adipose tissue (1), thereby obtaining a homogenized adipose tissue (1A) (refer to FIG. 8), wherein 1 g to 6 g of the adipose tissue (1) is arranged into the disposable enclosed vessel (21) to implement homogeneous mincing, while a preferred embodiment is that 3 g of the adipose tissue (1) is arranged into the disposable enclosed vessel (21) to implement homogeneous mincing. Preferably, revolution of the power unit (22) is 300-3000 rpm, and acting time of the power unit is 3-10 minutes; while a preferred revolution is 600-1500 rpm, and an optional revolution is 1200 rpm. In step (d), a reagent is added into the minced homogenized adipose tissue to implement a hydrolysis reaction, wherein the reagent is selected from one of the groups or combinations thereof formed by a trypsin, a dispase, a gelatase, a hyaluronidase, a collagenase type I or a collagenase type IV. Preferably, the present invention employs the collagenase type I or the collagenase type IV (Worthington Biochemical Corporation) as an embodiment, wherein a working concentration is 0.2 mg/ml to 20 mg/ml.

Preferably, the hydrolysis reaction is implemented in a constant temperature hybridization reaction oven (MO-01, Double Eagle Enterprise) for the whole process under conditions of 4-45 DEG C, 5 rpm-50 rpm and 0.5 h-24 h. The optional conditions are 37 DEG C, 15 rpm and 8 h. In step (e), a filtered fluid is obtained after slag of the adipose tissue treated via hydrolysis reaction is filtered, wherein a filtering mode can be a prior mode (such as filter membrane or filter screen) in any technical field so as to obtain the filtered fluid; then the filtered fluid is moved into a centrifugal tube with a volume of 50 ml to implement centrifugal separation, wherein the conditions for centrifugation are 400×g and 10 minutes. In step (f), a supernate after separation is removed so as to obtain a cell pellet, wherein the cell pellet is a stromal vascular fraction (SVF) cell consisting of a stromal cell, a blood cell, a vascular endothelial cell and an adipose tissue-derived stem cell.

Preferably, a step (g) of adding a phosphate buffer solution into the cell pellet, cleaning the cell pellet, and then centrifuging again so as to remove a supernate comprising blood and the reagent to obtain a cell pellet after being cleaned is further included after step (f). Preferably, a step (h) of arranging the cell pellet after being cleaned into a culture medium for culturing so as to obtain an amplified cell which is an undifferentiated adipose tissue-derived stem cell substantially is further included after step (g). Preferably, the adipose tissue-derived stem cell is expressing a cell surface antigen CD90, or CD105, or a combination thereof, and do not express CD45. Preferably, the culture medium comprises a basal culture medium (IMDM), a serum additive and a basic fibroblast growth factor-2 (FGF-2), wherein the serum additive is a fetal bovine serum with a volume percentage concentration of 2% to 10%, while a working concentration of the FGF-2 is 1 ng/ml to 20 ng/ml, among which 10 ng/ml is preferred.

Preferably, a step (i) of implementing cryopreservation on the amplified adipose tissue-derived stem cell for further applications such as clinical research, regenerative medicine research or development of cell and tissue engineering is included after step (h). Preferably, a step (i') of implementing induced differentiation on the amplified adipose tissue-derived stem cell so as to obtain a cell differentiated from the amplified adipose tissue-derived stem cell is included after step (h), wherein the cell differentiated includes one of an osteogenic cell, an adipose cell or a cartilage cell.

The invention further provides a cell bank, comprising the amplified adipose tissue-derived stem cell receiving cryopreservation in step (i).

Preferably, the term of [cryopreservation] used here usually refers to a preservation method of adding the cells into a cryoprotectant such as dimethyl sulfoxide (DMSO) or glycerol and cooling to a temperature below zero such as 80 DEG C below zero or 196 DEG C below zero (boiling point of liquid nitrogen). Cryopreservation may be implemented according to the methods and processes implemented by those skilled in the technique and will not be described herein any further since it is not the emphasis of the present invention (refer to Basic Cell Culture Process Second Edition written by Pollard, J. W. and Walker, J. M. in 1997 published by HummaPress; and Animal Cell Culture Fourth Edition written by Freshney, R. I. in 2000 published by Wiley-Liss).

The present invention provides a medicine composition, comprising one or a combination of the cell differentiated from the adipose tissue-derived stem cell in step (i') or the adipose tissue-derived stem cell which is undifferentiated substantially obtained.

Preferably, the medicine composition comprises the adipose tissue-derived stem cell, the cell differentiated from the adipose tissue-derived stem cell, a cell secretion secreted from the adipose tissue-derived stem cell, or one or a combination of cell extracts of the adipose tissue-derived stem cell and a suitable carrier/excipient that is therapeutically acceptable. Preferably, those skilled in the art know that principally all cases or diseases that are reported and pointed out in a research to be suitably treated via human mesenchymal stem cells can be treated by the medicine composition of the present invention, wherein stem cell transplantation can be effectively served as specific treatment purposes: for example, a stem cell generating a hematopoietic family may be used for replacing a hematopoietic system in marrow; a stem cell generating a mesenchymal family may be used for repairing musculoskeletal disorders, a stem cell differentiated into an epithelial family may be used for repairing surface damage; and a stem cell differentiated into a nerve cell family may be used for treating neurodegenerative diseases.

Preferably, the adipose tissue-derived stem cells obtained via the method of the present invention at least express a cell surface antigen CD90 or CD105, or a combination thereof, and do not express CD45; moreover, the adipose tissue-derived stem cells have the capacities of being differentiated into bone, cartilage and fat, so that the adipose tissue-derived stem cells obtained via the method of the present invention become a rich source for pluripotent stem cells possessing differentiation potentials; moreover, the adipose tissue-derived stem cells possess potential clinical applicability for cell therapy. Therefore, the adipose tissue-derived stem cells obtained via the method of the present invention can be applied in a material for cell therapy, regenerative medicine or cell and tissue engineering; for example, the adipose tissue-derived stem cells may be used for treating or slowing degenerated diseases, organ regeneration or tissue regeneration in the future.

The embodiment of employing the lump adipose tissue obtained from the surgery excision of the human being has been described for illustrating the embodiments of the present invention; however, the present invention is not limited by the following embodiments.

[Experiment 1] Stromal Vascular Fraction Cells in Adipose Tissues are Separated.

1. Cells and cell survival rate of stromal vascular fraction cells obtained from adipose tissues of per gram The experiment is implemented in a Gene and Stem Cell Regeneration Laboratory affiliated to Buddhist Tzu Chi General Hospital and passing through ISO14644 Class 7 certificate, and operating personnel in the Laboratory is implemented in accordance with Good Tissue Practice (GTP). Abdominal subcutaneous adipose tissue lump specimens of 11 donors from Min-Sheng General Hospital are collected, wherein each specimen is about 30 g, and the specimens collected in the present invention are approved by Internal Examination Committee of Min-Sheng General Hospital. The specimens of two donors are employed to implement the experiment firstly, wherein weights of the specimens of the first donor are divided into six groups which respectively include 1 g, 2 g, 3 g, 4 g, 5 g and 6 g, and weights of the specimens of the second donor are divided into five groups which respectively include 1 g, 2 g, 3 g, 4 g and 5 g to implement separation, wherein a separation step is as previously mentioned, and thus will not be described herein any further. Determination part of the cell survival rate is implemented as follows: after the stromal vascular fraction cells obtained is stained via propidium iodide (PI), the stromal vascular fraction cells separated out from each group are calculated by an automatic cell counter (Adam-MC, NanoEnTek). In addition, determination of the stromal vascular fraction cells is implemented as follows: a cytomembrane is broken up via a cytomembrane dissolution buffer solution, and then an DNA of a cell nucleus is stained by propidium iodide (PI), thus avoiding red blood cells included in the stromal vascular fraction cells from affecting counting the stromal vascular fraction cells, so as to obtain a more precise cell determination value.

1.1 Experimental Result

Figure 2A:
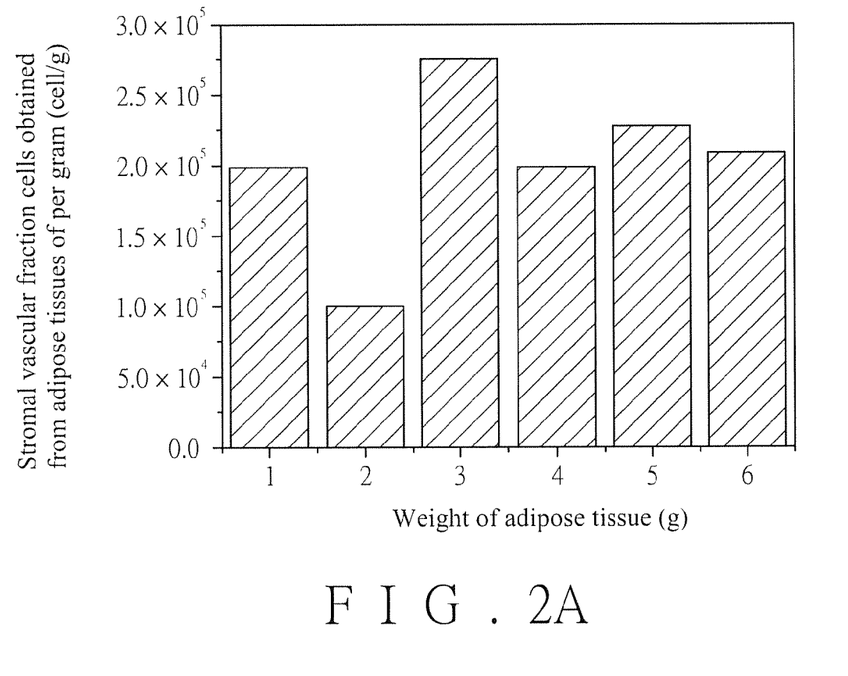
FIG. 2A is a comparison chart of stromal vascular fraction cells obtained from adipose tissues of different grams of a first donator in the present invention.
Figure 2B:
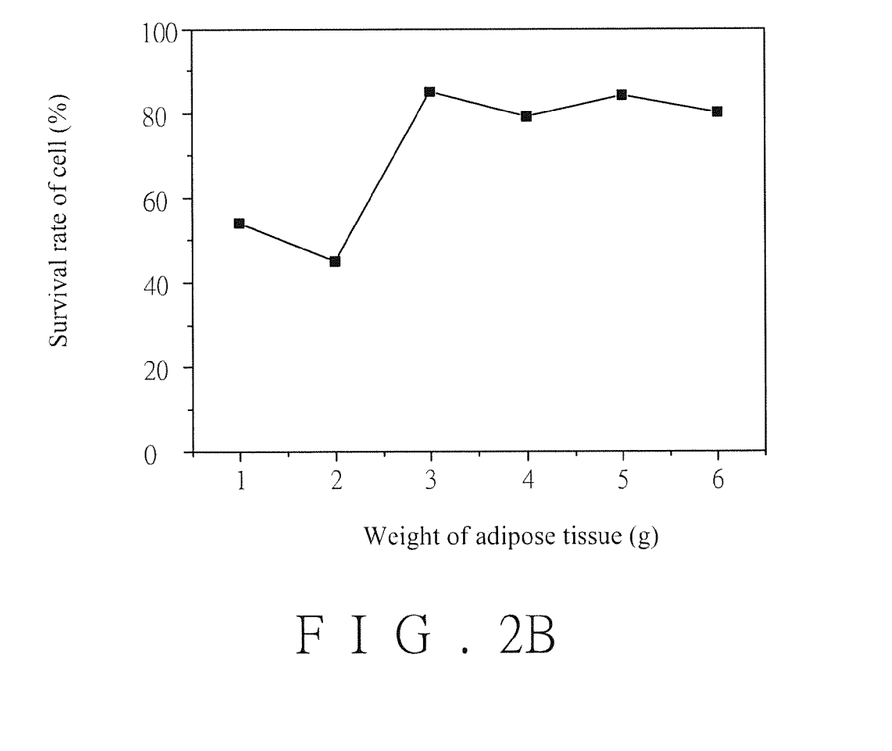
FIG. 2B is a survival rate comparison chart of the stromal vascular fraction cells obtained from the adipose tissues of different grams of the first donator in the present invention.
Figure 2C:
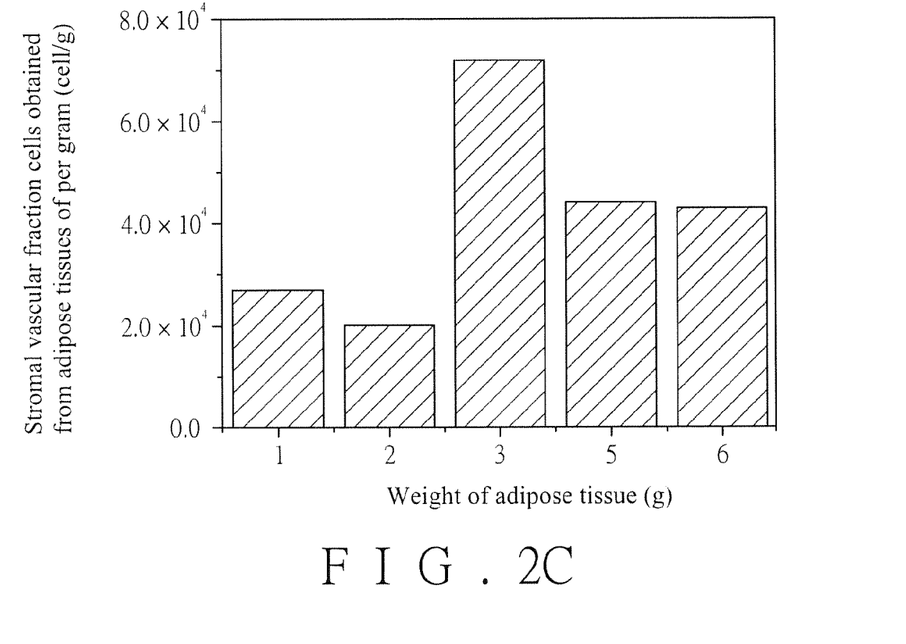
FIG. 2C is a comparison chart of stromal vascular fraction cells obtained from adipose tissues of different grams of a second donator in the present invention.
Figure 2D:
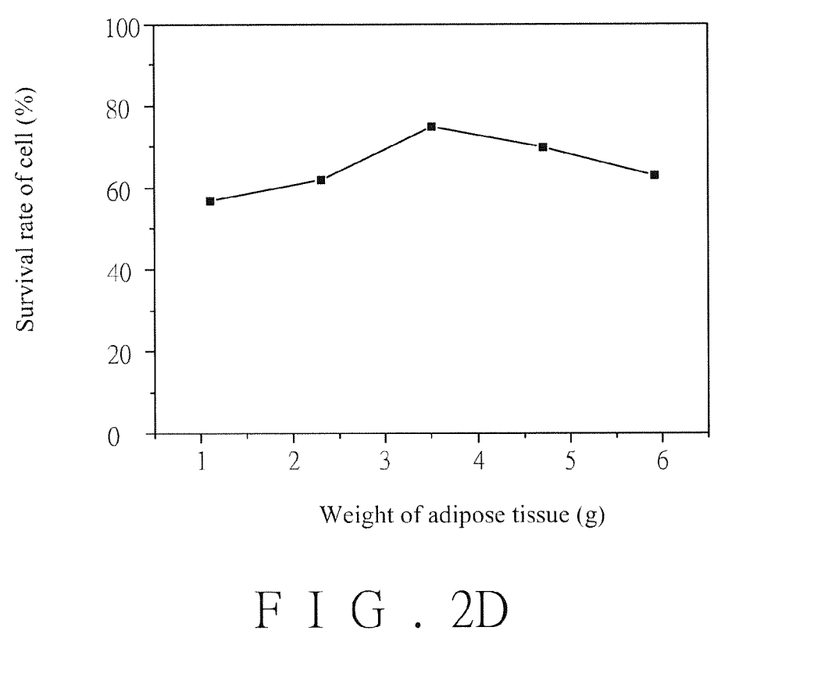
FIG. 2D is a survival rate comparison chart of the stromal vascular fraction cells obtained from the adipose tissues of different grams of the second donator in the present invention.

The experimental data is statistically analyzed via t-test of a Microsoft Excel software, by taking $p<0.05$ as a significance level, and a result is quantified into a statistical chart. Referring to FIG. 2A which is a comparison chart of stromal vascular fraction cells obtained from adipose tissues of different grams of the first donor, the result shows that the stromal vascular fraction cells obtained from adipose tissues of per gram of the group in which 3 g of adipose tissues are arranged into a disposable enclosed vessel with a volume of 15 ml to implement homogeneous mincing exceed $2.5 \times 10^5$, which is the highest among the groups. Continuously referring to FIG. 2B which is a survival rate comparison chart of the stromal vascular fraction cells obtained from the adipose tissues of different grams of the first donor, the result shows that the survival rate of the stromal vascular fraction cells of the group in which 3 g of adipose tissues are arranged into a disposable enclosed vessel with a volume of 15 ml to implement homogeneous mincing exceeds 80%, which is highest among the groups. Additionally referring to FIG. 2C which is a comparison chart of stromal vascular fraction cells obtained from adipose tissues of different grams of the second donor, the result shows that the stromal vascular fraction cells obtained from adipose tissues of per gram of the group in which 3 g of adipose tissues are similarly arranged into a disposable enclosed vessel with a volume of 15 ml to implement homogeneous mincing exceed $7.0 \times 10^4$, which is the highest among the groups. Continuously referring to FIG. 2D which is a survival rate comparison chart of the stromal vascular fraction cells obtained from the adipose tissues of different grams of the second donor, the result shows that the survival rate of the stromal vascular fraction cells of the group in which 3 g of adipose tissues are arranged into a disposable enclosed vessel with a volume of 15 ml to implement homogeneous mincing is about 90%, which is higher among the groups. From the experiments, arranging 3 g of adipose tissue lumps into the disposable enclosed vessel with a volume of 15 ml to implement homogeneous mincing is a preferred condition, which can obtain preferred stromal vascular fraction cells and a preferred survival rate of the stromal vascular fraction cells from the adipose tissue of per gram.

2. Comparison Between Influences of Surgical Scissors and a Disposable Homogenizer Under Different Revolution Conditions on the Cells and the Survival Rate of the Cells.

The adipose tissue lumps of the first donor are employed in the experiment and divided into five groups including a surgical scissor group, a revolution 400 group, a revolution 600 group, a revolution 1200 group and a revolution 1500 group to implement the step of homogeneous mincing on the adipose tissues, so as to facilitate subsequent separation of the stromal vascular fraction cells, while the subsequent separation step is the same as the foregoing method; moreover, both the method for determining the survival rate of the cells and the method for determining the stromal vascular fraction cells are both the same with the foregoing experiment, and thus will not be described herein any further.

2.1 Experimental Result

Figure 3A:
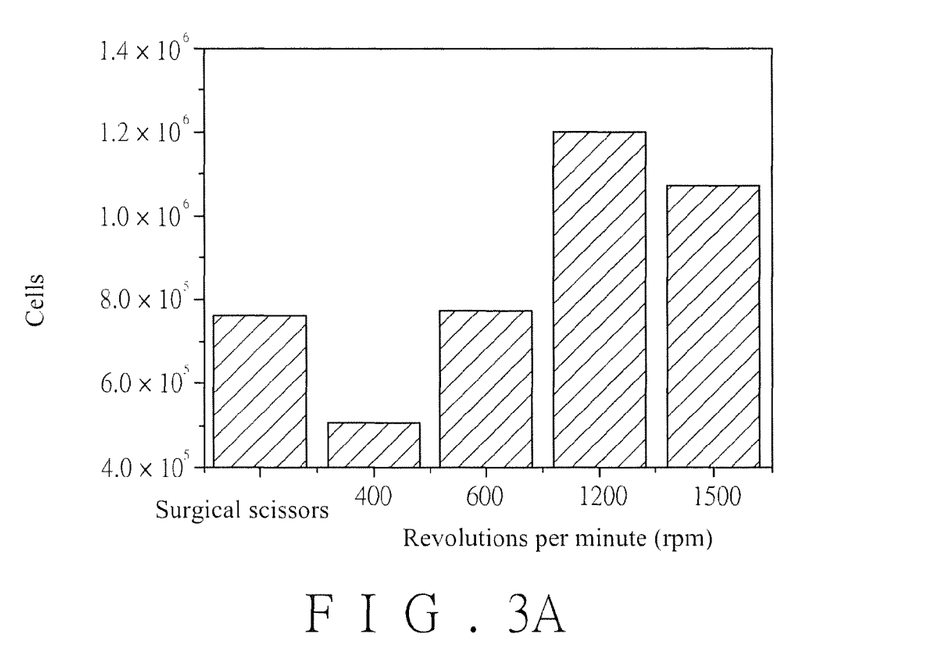
FIG. 3A is a comparison chart of stromal vascular fraction cells obtained from adipose tissues treated by surgical scissors and obtained from adipose tissues treated by a homogenizer under different revolution conditions in the present invention.
Figure 3B:
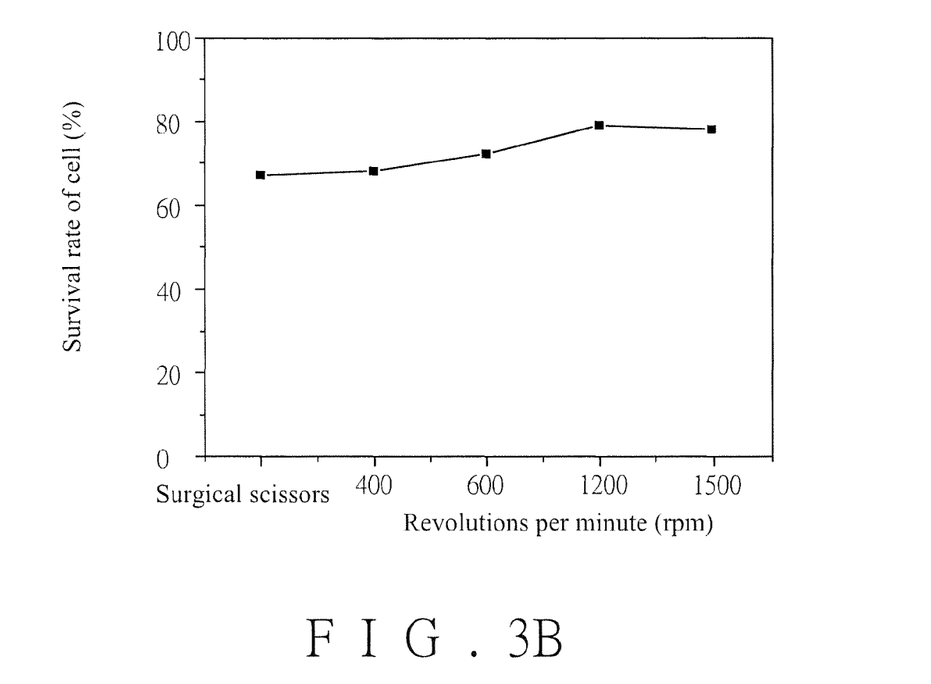
FIG. 3B is a survival rate comparison chart of the stromal vascular fraction cells obtained from the adipose tissues treated by the surgical scissors and obtained from the adipose tissues treated by the homogenizer under different revolution conditions in the present invention.

The experimental data is statistically analyzed via t-test of the Microsoft Excel software, by taking $p<0.05$ as a significance level, and a result is quantified into a statistical chart. Referring to FIG. 3A which is a comparison chart of stromal vascular fraction cells obtained from adipose tissues treated by surgical scissors and obtained from adipose tissues treated by a homogenizer under different revolution conditions, the result shows that $1.2\times10^6$ cells are obtained by the homogenizer revolution 1200 group, which is highest among the groups, and is far more than the cells obtained from the surgical scissor group. Continuously referring to FIG. 3B which is a survival rate comparison chart of the stromal vascular fraction cells obtained from the adipose tissues treated by the surgical scissors and obtained from the adipose tissues treated by the homogenizer under different revolution conditions, the result shows that the survival rate of the stromal vascular fraction cells obtained by the group in which the revolution of the homogenizer is 1200 is about 80%, which is higher among the groups, while the survival rate of the stromal vascular fraction cells obtained by the surgical scissor group is no more than 70%. Thus it can be seen from the experimental result that using the homogenizer in the method of the present invention to replace the adipose tissues in the prior art to implement homogeneous mincing on the adipose tissue lumps not only can increase the stromal vascular fraction cells obtained, but also can not reduce the survival rate of the stromal vascular fraction cells obtained.

3. Comparison Between the Total Cell Yield Ratio and the Survival Rate Ratio of the Stromal Vascular Fraction Cells Treated by the Disposable Homogenizer and that of the Stromal Vascular Fraction Cells Treated by the Surgical Scissors.

Abdominal subcutaneous adipose tissue lump specimens of 9 donators are employed in the experiment and are respectively divided into a surgical scissor group and a homogenizer revolution 1200 group; 3 g of adipose tissue lumps from each donator are employed to receive homogeneous mincing operation, so as to facilitate subsequent separation of the stromal vascular fraction cells; moreover, the subsequent separation steps are the same with the foregoing method. Both the method for determining the survival rate of the cells and the method for determining the stromal vascular fraction cells are both the same with the foregoing experiment, and thus will not be described herein any further. However, a result obtained is represented in a way of a ratio (times) of the homogenizer/surgical scissor.

3.1 Experimental Result

Figure 4A:
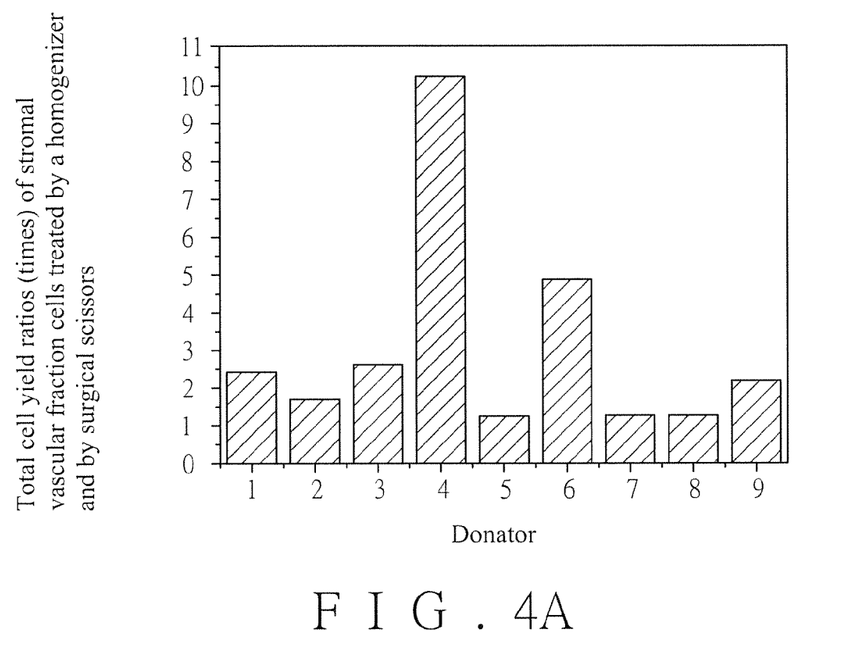
FIG. 4A is a comparison chart for total cell yield ratios of stromal vascular fraction cells obtained from adipose tissues of nine donators minced by a homogenizer and by surgical scissors in the present invention.
Figure 4B:
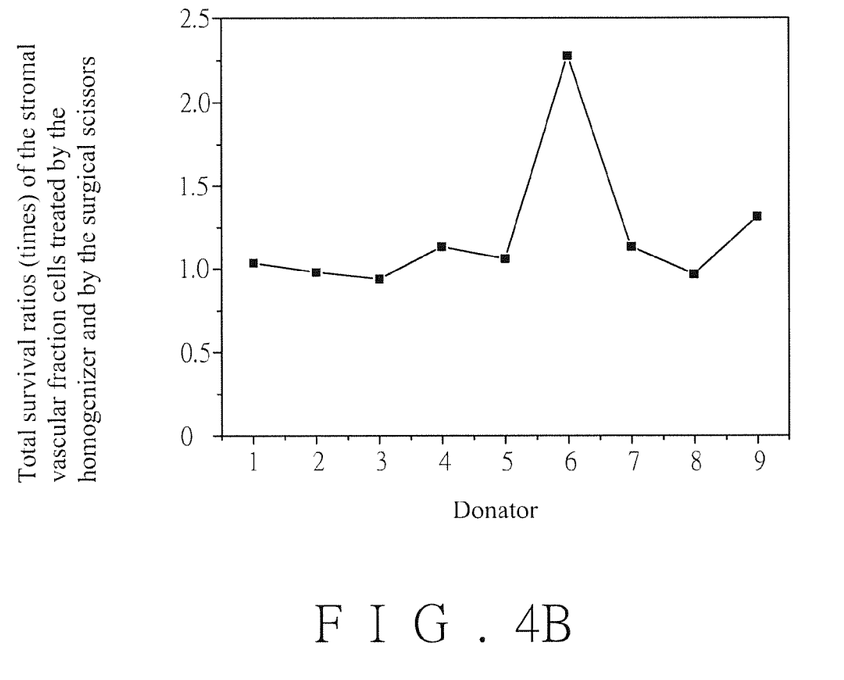
FIG. 4B is a comparison chart for survival ratios of the stromal vascular fraction cells obtained from the adipose tissues of the nine donators minced by the homogenizer and by the surgical scissors in the present invention.

The experimental data is statistically analyzed via t-test of the Microsoft Excel software, by taking $p<0.05$ as a significance level, and a result is quantified into a statistical chart. Referring to FIG. 4A which is a comparison chart for total cell yield ratios (times) of stromal vascular fraction cells obtained from adipose tissues of nine donators minced by a homogenizer and by surgical scissors, the result shows that the total cell yield ratios (times) of the stromal vascular fraction cells obtained from the adipose tissues of nine donators minced by the homogenizer and by the surgical scissors is between 1.3 times and 10.2 times, wherein the ratio is different due to individuals. Continuously referring to FIG. 4B which is a comparison chart for survival ratios (times) of the stromal vascular fraction cells obtained from the adipose tissues of the nine donators minced by the homogenizer and by the surgical scissors, the result shows that the survival ratios (times) of the stromal vascular fraction cells obtained from the adipose tissues of nine donators minced by the homogenizer and by the surgical scissors is between 0.9 times and 2.3 times, wherein the ratio is different due to individuals. Thus it can be seen that using the homogenizer in the method of the present invention to replace the surgical scissors in the prior art to implement homogeneous mincing on the adipose tissue lumps not only can increase the stromal vascular fraction cells obtained, but also can not reduce the survival rate of the stromal vascular fraction cells obtained.

4. Comparison Between the Total Cell Yield Ratio and the Survival Rate Ratio of the Adipose Tissue-Derived Stem Cells Obtained by the Disposable Homogenizer and that of the Adipose Tissue-Derived Stem Cells Obtained by the Surgical Scissors.

The grouping method of the experiment is same to the method 3 of the [Experiment 1], and the stromal vascular fraction cells obtained from each group are arranged in a culture medium for 5 days so as to obtain the adipose tissue-derived stem cells; moreover, influences of the homogenizer and the surgical scissors on the total cell yield ratio and the survival rate ratio of the adipose tissue-derived stem cells are analyzed. The culture medium comprises basal culture mediums (IMDMs, GIBCO-Invitrogen) of a fetal bovine serum additive (GIBCO-Invitrogen) and a basic fibroblast growth factor-2 (FGF-2, R&D Systems), wherein the volume percentage concentration of the fetal bovine serum additive is 2% to 10%, while a working concentration of the FGF-2 is 10 ng/ml. The stromal vascular fraction cells of each group are cultured in a cell culture tray with a cell density of 10000 cells/cm$^2$); moreover, all the cells are cultured in an incubator (Forma Series II Model 3110, Thermo) under a circumstance of a temperature of 37 DEG C, a $CO_2$ partial pressure of 5% and a humidity of 95%; in addition, the culture medium is replaced in every 3 days. The adipose tissue-derived stem cells after being cultured for 5 days are cleaned once by a phosphate buffered solution (PBS), acted in a Trypsin-EDTA (GIBCO-Invitrogen) solution for 5 minutes under a temperature of 37 DEG C; then the cells which are not sufficiently acted are carefully removed by a cell scraper, added into the culture medium comprising the fetal bovine serum in equal proportions and enzymosis activity of Trypsin. Determination of the cell survival rate is counted by a cell counter (Vi-CELL AS, Beckman Coulter). The survival cells are distinguished from dead cells by 0.4% Trypan-blue (GIBCO-Invitrogen). Parameters for judging live adipose-derived stem cells during counting are set as: 100 images, 10-30 μm in size, 75% spot brightness and 5% spot area. In addition, the yields of the adipose-derived stem cells in each group are counted by using a doubling time (DT) formula, and $DT=t/(3.32[\log_{10}N_t-\log_{10}N_0])$, wherein $N_t$ refers to the latest density of the cells, while $N_0$ refers to the initial density of the cells. In the experiment, a result obtained is represented in a way of a ratio (times) of the homogenizer/surgical scissor.

4.1 Experimental Result

Figure 5A:
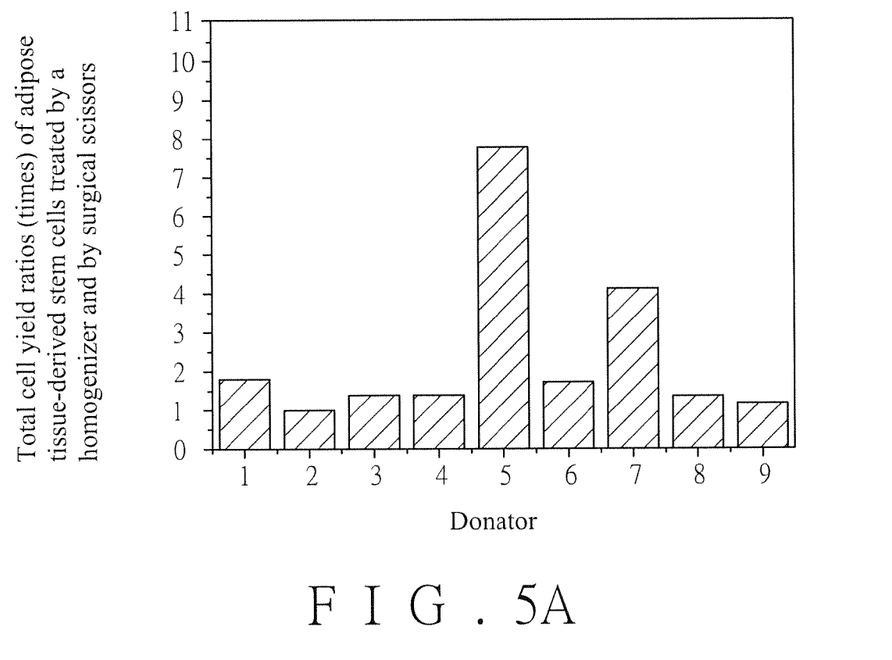
FIG. 5A is a comparison chart for total cell yield ratios of adipose tissue-derived stem cells obtained from adipose tissues of nine donators minced by a homogenizer and by surgical scissors in the present invention.
Figure 5B:
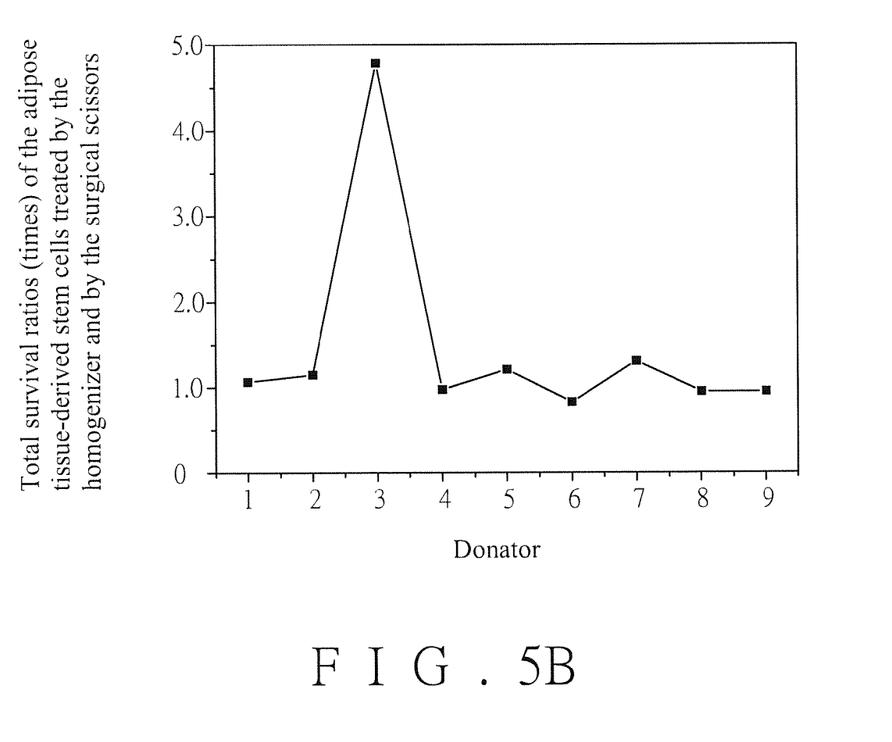
FIG. 5B is a comparison chart for survival ratios of the adipose tissue-derived stem cells obtained from the adipose tissues of the nine donators minced by the homogenizer and by the surgical scissors in the present invention.

The experimental data is statistically analyzed via t-test of the Microsoft Excel software, by taking $p<0.05$ as a significance level, and a result is quantified into a statistical chart. Referring to FIG. 5A which is a comparison chart for total cell yield ratios of adipose tissue-derived stem cells obtained from adipose tissues of nine donators minced by a homogenizer and by surgical scissors in the present invention, the result shows that the total cell yield ratios (times) of the adipose tissue-derived stem cells obtained from the adipose tissues of nine donators minced by the homogenizer and by the surgical scissors is between 1.2 times and 7.8 times, wherein the ratio is different due to individuals. Continuously referring to FIG. 5B which is a comparison chart for survival ratios (times) of the adipose tissue-derived stem cells obtained from the adipose tissues of the nine donators minced by the homogenizer and by the surgical scissors, the result shows that the survival ratios (times) of the adipose tissue-derived stem cells obtained from the adipose tissues of nine donators minced by the homogenizer and by the surgical scissors is between 0.8 times and 4.8 times, wherein the ratio is different due to individuals. Thus it can be seen that using the homogenizer in the method of the present invention to replace the surgical scissors in the prior art to implement homogeneous mincing on the adipose tissue lumps not only can increase the adipose tissue-derived stem cells obtained, but also can not reduce the survival rate of the adipose tissue-derived stem cells.

5. Relation Between a Body Mass Index (BMI) of a Donator and Yields of Stromal Vascular Fraction Cells/Adipose Tissue-Derived Stem Cells from Adipose Tissues of Per Gram (Cell/g)

In the experiment, the body mass indexes of the nine donators are combined with the experimental results obtained by being treated by the disposable homogenizer and by the surgical scissors in the prior art, so as to further analyze the relation between the body mass index and the yields of the stromal vascular fraction cells/adipose tissue-derived stem cells from the adipose tissues of per gram.

5.1 Experimental Result

Figure 6A:
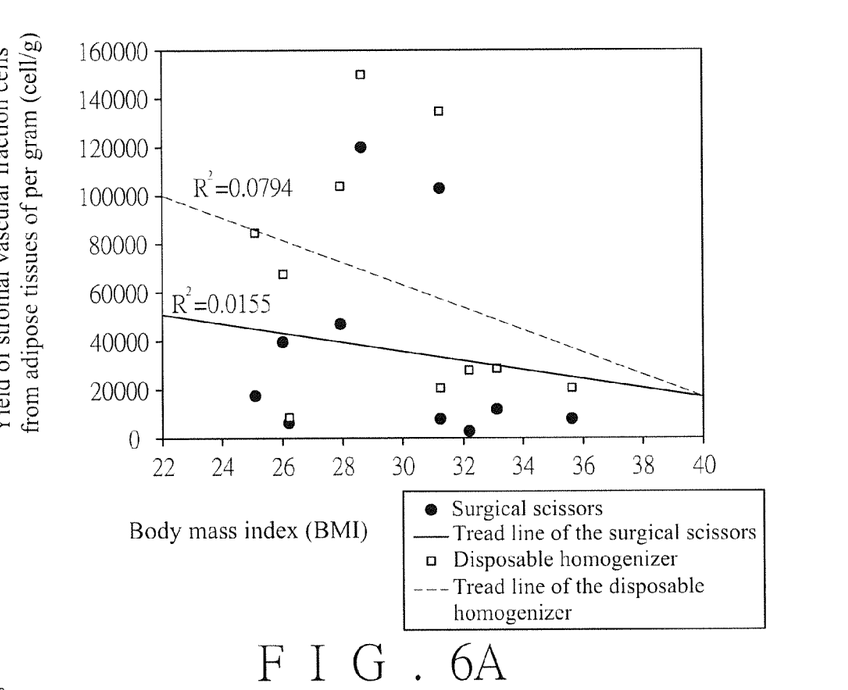
FIG. 6A is a diagram for relation between a body mass index of a donator and a yield of stromal vascular fraction cells from adipose tissues of per gram (cell/g) in the present invention.
Figure 6B:
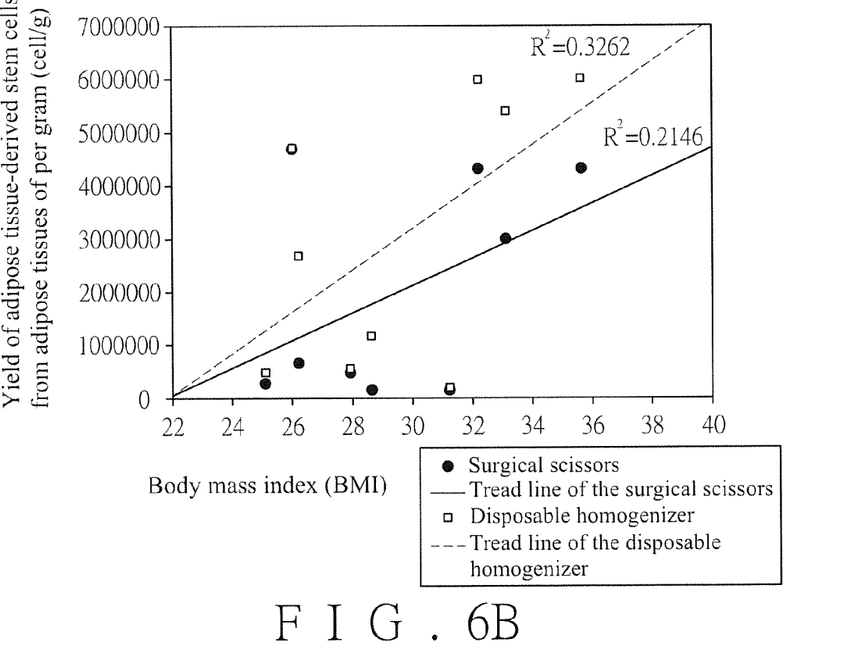
FIG. 6B is a diagram for relation between a body mass index of a donator and a yield of adipose tissue-derived stem cells from adipose tissues of per gram (cell/g) in the present invention.

Referring to FIG. 6A which is a diagram for relation between the body mass index of the nine donators and a yield of stromal vascular fraction cells from adipose tissues of per gram (cell/g). Each point of the disposable homogenizer group of the present invention in the FIG. 6A shows a trend dotted line that $R^2$ is 0.0794 via regression computation; while each point of the surgical scissor group shows a trend full line that $R^2$ is 0.0155 via regression computation. Thus it can be seen that the method of the present invention can obtain more stromal vascular fraction cells from the adipose tissues of per gram than that of the surgical scissor group when the body mass index of the donator is relatively lower. Continuously referring to FIG. 6B which is a diagram for relation between the body mass index of the nine donators and a yield of the adipose tissue-derived stem cells from the adipose tissues of per gram (cell/g), each point of the disposable homogenizer group of the present invention in the FIG. 6B shows a trend dotted line that $R^2$ is 0.3262 via regression computation; while each point of the surgical scissor group shows a trend full line that $R^2$ is 0.2146 via regression computation. Thus it can be seen that the method of the present invention can obtain more adipose tissue-derived stem cells from the adipose tissues of per gram than that of the surgical scissor group when the body mass index of the donator is relatively higher.

[Experiment 2] Analysis and Applications of Adipose Tissue-Derived Stem Cells Obtained Via the Method of the Present Invention 1. Cell Surface Antigen Analysis of Typical Mesenchymal Stem Cells In the experiment, a flow cytometer (FACSCalibur, Becton Dickinson) is employed to implement determination of the cell surface antigens. After the adipose tissue-derived stem cells obtained via the method of the present invention are subcultured, a Trypsin-EDTA solution is used to act for 5 minutes under a temperature of 37 DEG C for adhesion, cleaned by a phosphatic buffer solution, recycled and centrifuged; then a supernate is removed to obtain a cell pellet, and then is re-dissolved into proper phosphatic buffer solution; different antigens are respectively stained via corresponding immunofluorescence primary antibodies comprising such antibodies (Becton Dickinson) as CD13, CD34, CD44, CD45, CD73, CD90, CD105, $\beta_2$ microglobulin (B2M) and HLA-DR. After the antigens are stained for 15 m under a room temperature in a dark place and proper phosphatic buffer solution is added, and then is analyzed on the flow cytometer; after date is collected by the flow cytometer, analysis is implemented by an analysis software of the flow cytometer (FACSCalibur, Becton Dickinson), wherein a negative control group omits the step of staining via the primary antibodies.

1.1 Experimental Result

Referring to table 1 as follows, a result shows that expressions of the cell surface antigens of the adipose tissue-derived stem cells obtained via the method of the present invention are CD13+, CD34−, CD44+, CD45−, CD73+, CD90+ and CD105+, which expressions of the cell surface antigens are similar to typical mesenchymal stem cells. That is to say the adipose tissue-derived stem cells obtained via the method of the present invention still maintain the surface antigen characteristics which are similar to typical mesenchymal stem cells.

TABLE I

| Cell Surface Antigen Analysis | |
|---|---|
| Cell Surface Antigen | Percentage (%) |
| CD13 | 100.0 |
| CD34 | 2.0 |
| CD44 | 99.9 |
| CD45 | 0.1 |
| CD73 | 99.9 |
| CD90 | 100.0 |
| CD105 | 97.4 |
| HLA-DR | 0.3 |

2. Differentiation of Adipose Tissue-Derived Stem Cells

A literature reports that the adipose tissue-derived stem cells have a capable of being differentiated into mesoblastic cells such as adipose cells and osteogenic cells. In the experiment, the adipose tissue-derived stem cells after proper induced differentiation culturing are differentiated into osteogenic cells, cartilage cells and adipose cells, so as to determine whether the adipose tissue-derived stem cells obtained via the method of the present invention still have a stem cell multifunctional differentiation capacity. The induced differentiation experiment in the present invention is based on a stem cell induced differentiation system (Kanda et al., 2011; Song et al., 2010) in the prior art that is generally used, and thus will not be described herein any further. The major objective of the experiment is to determine whether the adipose tissue-derived stem cells obtained via the method of the present invention still have the stem cell multifunctional differentiation capacity. The differentiated bone cells are stained via an alkaline phosphatase (ALP), wherein the alkaline phosphatase is an important indicator for differentiating a mature osteoblast. The staining method thereof is implemented according to the staining technology (Yoshimura et al., 2011) of the prior art, and thus will not be described herein any further. Moreover, Vonkossa staining of the prior art is also implemented so as to determine whether calcium phosphate exists. The differentiated cartilage cells are stained by Alcian blue so as to determine whether proteoglycan possessed in a cartilage tissue exists (Song et al., 2010). The differentiated adipose cells are stained by Oil red O so as to determine whether Lipid vacuoles exists (Kanda et al., 2011).

2.1 Experimental Result

Figure 7A:
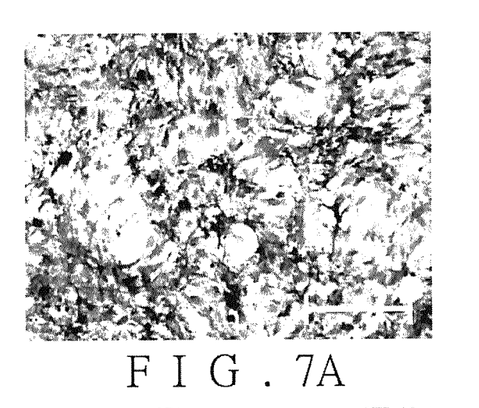
FIG. 7A is a result chart of adipose tissue-derived stem cells induced and differentiated into born cells and stained by alkaline phosphatase in the present invention.
Figure 7B:
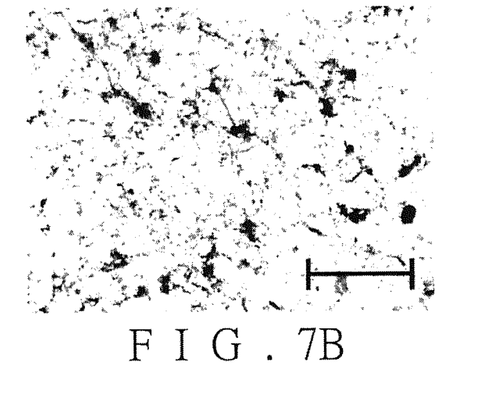
FIG. 7B is a result chart of the adipose tissue-derived stem cells induced and differentiated into born cells and stained by VON KOSSA in the present invention.
Figure 7C:
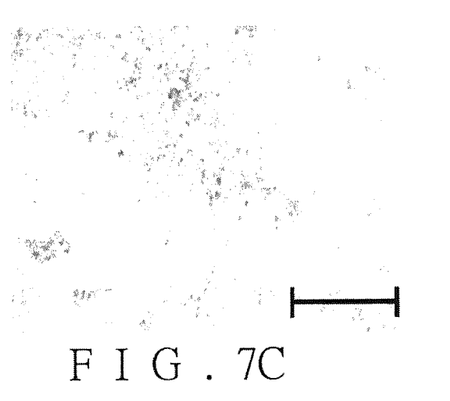
FIG. 7C is a result chart of the adipose tissue-derived stem cells induced and differentiated into cartilage cells and stained by alcian blue in the present invention.
Figure 7D:
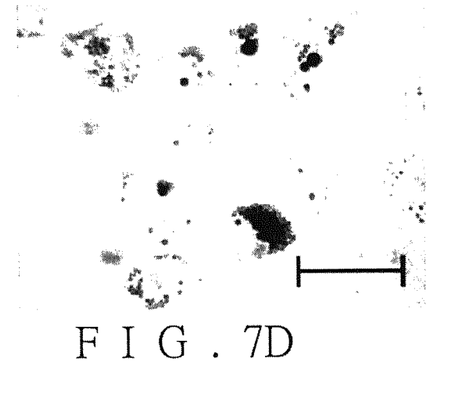
FIG. 7D is a result chart of the adipose tissue-derived stem cells induced and differentiated into adipose cells and stained by oil red O in the present invention.

Referring to FIG. 7A which is an alkaline phosphatase staining result with a proportional scale of 500 μm, the adipose tissue-derived stem cells obtained via the method of the present invention are induced and differentiated into bone cells and possess parts showing black crystals after being stained by alkaline phosphatase, which is namely representing existence of the alkaline phosphatase. Continuously referring to FIG. 7B which is a Von-kossa staining result with a proportional scale of 500 μm, it can be found that black or dark brown calcium phosphate crystals are shown, which illustrates again that the adipose tissue-derived stem cells obtained via the method of the present invention have a capacity of being differentiated into bone cells. Referring to FIG. 7C which is an Alcian blue staining result with a proportional scale of 500 μm, it can be found that a blue proteoglycan staining result is shown, which represents that the adipose tissue-derived stem cells obtained via the method of the present invention have a capacity of being differentiated into cartilage cells. Continuously referring to FIG. 7C which is an Oil red O staining result with a proportional scale of 500 μm, it can be found that a red lipid vacuole staining result is shown, which represents that the adipose tissue-derived stem cells obtained via the method of the present invention have a capacity of being differentiated into adipose cells. It can be known from the above differentiation results that the adipose tissue-derived stem cells obtained via the method of the present invention do have the stem cell multifunctional differentiation capacity.

It can be seen from the above experimental results that using the homogenizer in the method of the present invention to replace the surgical scissors in the prior art to implement homogeneous mincing on the adipose tissue lumps not only can increase the adipose tissue-derived stem cells obtained, but also can not reduce the survival rate of the adipose tissue-derived stem cells. In addition, the adipose tissue-derived stem cells obtained via the method of the present invention do have the cell surface antigens of mesenchymal stem cells and the multifunctional differentiation capacity, so that the adipose tissue-derived stem cells obtained via the method of the present invention become a rich source for pluripotent stem cells possessing differentiation potentials; moreover, the adipose tissue-derived stem cells possess potential clinical applicability for cell treatment. Therefore, the adipose tissue-derived stem cells can be applied for preparing a medicine composition so as to be applied on a material for cell therapy, regenerative medicine or cell and tissue engineering; for example, the adipose tissue-derived stem cells may be used for treating or slowing degenerated diseases, tissue damage repairing, organ regeneration and tissue regeneration in the future. Moreover, cryopreservation can also be implemented on the adipose tissue-derived stem cells and a cell bank can be established for subsequent applications such as clinical research, regenerative medicine research or development of cell and tissue engineering.

The preferred embodiments above describe the present invention, but are not intended to limit the present invention. Any person skilled in the art may make some alternations and amendments without departing from the spirit and scope of the present invention. Therefore, the protection scope of the present invention shall be subject to the determined patent scope of applications attached hereafter.

What is claimed is:

1. A method for isolating live, stromal vascular fraction (SVF) cells in vitro from adipose tissues, comprising the steps as follows:

step (a) providing an adipose tissue;

step (b) arranging the adipose tissue into an enclosed vessel of a cutting device, wherein the cutting device is a disposable homogenizer comprising a power unit;

step (c) applying an acting force on the enclosed vessel by the cutting device to enable a preset cutting tool in the enclosed vessel to implement rapid and homogeneous mincing on the adipose tissue in a closed environment, thereby obtaining a homogenized adipose tissue, wherein a relative centrifugal force of the cutting tool is 16-25×g;

step (d) adding a reagent into the homogenized adipose tissue to implement a hydrolysis reaction;

step (e) filtering and centrifugally separating the homogenized adipose tissue treated via the hydrolysis reaction; and step (f) removing a supernate after the centrifugal separation so as to obtain a cell pellet, which contains isolated stromal vascular fraction (SVF) cells.

2. The method for isolating live, stromal vascular fraction (SVF) cells in vitro from adipose tissues according to claim 1, wherein a step of cleaning the adipose tissue via a phosphate buffer solution is included before step (a).

3. The method for isolating live, stromal vascular fraction (SVF) cells in vitro from adipose tissues according to claim 1, wherein the adipose tissue in step (a) is a lump adipose tissue obtained from surgery excision of a mammal.

4. The method for isolating live, stromal vascular fraction (SVF) cells in vitro from adipose tissues according to claim 3, wherein the mammal is a human being.

5. The method for isolating live, stromal vascular fraction (SVF) cells in vitro from adipose tissues according to claim 1, wherein the disposable homogenizer comprises a disposable enclosed vessel, and the inside of the disposable enclosed vessel is provided with a cutting tool.

6. The method for isolating live, stromal vascular fraction (SVF) adipose tissues according to claim 5, wherein the homogeneous mincing in step (c) is performed by arranging 1 g to 6 g of adipose tissues into the disposable enclosed vessel with a volume of 15 ml to implement rapid and homogeneous mincing.

7. The method for isolating live, stromal vascular fraction (SVF) cells in vitro from adipose tissues according to claim 6, wherein the homogeneous mincing in step (c) is performed by arranging 3 g of adipose tissues into the disposable enclosed vessel with a volume of 15 ml to implement rapid and homogeneous mincing.

8. The method for isolating live, stromal vascular fraction (SVF) cells in vitro from adipose tissues according to claim 7, wherein an acting time of the power unit is 3-10 minutes.

9. The method for isolating live, stromal vascular fraction (SVF) cells in vitro from adipose tissues according to claim 1, wherein the reagent in step (d) is selected from the group consisting of a trypsin, a dispase, a gelatase, a hyaluronidase, a collagenase type I, a collagenase type IV and combinations thereof.

10. The method for isolating live, stromal vascular fraction (SVF) cells in vitro from adipose tissues according to claim 1, wherein the hydrolysis reaction in step (d) is implemented in a constant temperature hybridization reaction oven for the whole process under conditions of 4-45 DEG C., 5 rpm-50 rpm and 0.5 h-24 h.

11. The method for isolating live, stromal vascular fraction (SVF) cells in vitro from adipose tissues according to claim 10, wherein the preferred conditions are 37 DEG C., 15 rpm and 8 h.

12. The method for isolating live, stromal vascular fraction (SVF) cells in vitro from adipose tissues according to claim 1, wherein the conditions for centrifugation in step (e) are 400×g and 10 minutes.

13. The method for isolating live, stromal vascular fraction (SVF) cells in vitro from adipose tissues according to claim 1, wherein step (e) comprises a step of moving a filtered fluid obtained after filtering the homogenized adipose tissue treated via the hydrolysis reaction into a centrifugal tube, so as to implement centrifugal separation.

14. The method for isolating live, stromal vascular fraction (SVF) cells in vitro from adipose tissues according to claim 1, wherein after step (f), performing a step (g) of adding the phosphate buffer solution into the cell pellet, cleaning the cell pellet, and then centrifuging again so as to remove a supernate comprising blood and the reagent to obtain a cleaned cell pellet.

15. The method for isolating live, stromal vascular fraction (SVF) cells in vitro from adipose tissues according to claim 14, wherein after being cleaned in step (g), a step (h) of arranging the cell pellet into a culture medium for culturing so as to obtain amplified cells.

16. The method for isolating live, stromal vascular fraction (SVF) cells in vitro from adipose tissues according to claim 15, wherein the culture medium comprises a basal culture medium (IMDM), a serum additive and a fibroblast growth factor-2 (FGF-2).

17. The method for isolating live, stromal vascular fraction (SVF) cells in vitro from adipose tissues according to claim 16, wherein the serum additive is a fetal bovine serum with a volume percentage concentration of 2% to 10%, and a concentration of the FGF-2 is 1 ng/ml to 20 ng/ml.

18. The method for isolating live, stromal vascular fraction (SVF) cells in vitro from adipose tissues according to claim 15, wherein the amplified cell is an adipose tissue-derived stem cell which is substantially undifferentiated.

19. The method for isolating live, stromal vascular fraction (SVF) cells in vitro from adipose tissues according to claim 18, wherein the adipose tissue-derived stem cell at least shows a cell surface antigen CD90, or CD 105 or a combination thereof, and does not show CD45.

20. A method for cell therapy, regenerative medicine or cell and tissue engineering, comprising;
making an adipose tissue-derived stem cell according to the method of claim 19; and
applying the adipose tissue-derived stem cells singly or in combination as a material for cell therapy, regenerative medicine or cell and tissue engineering.

21. A method for treating one or a combination of degenerated diseases, tissue damage repair, organ regeneration or tissue regeneration, comprising;
making an adipose tissue-derived stem cell according to the method of claim 18;
and
preparing medicinal compositions for cell therapy from the adipose tissue-derived stem cell.

22. A method for establishing a cell bank, comprising;
making an amplified adipose tissue-derived stem cells by the method according to claim 18; and
implementing cryopreservation on the amplified adipose tissue-derived stem cell.

23. The method for isolating live, stromal vascular fraction (SVF) cells in vitro from adipose tissues according to claim 18, wherein a step (i') of implementing induced differentiation on the amplified adipose tissue-derived stem cell so as to obtain a cell differentiated from the amplified adipose tissue-derived stem cell is included after step (h).

24. The method for isolating live, stromal vascular fraction (SVF) cells in vitro from adipose tissues according to claim 23, wherein the cells differentiated from the amplified adipose tissue-derived stem cells include one of an osteogenic cell, an adipose cell or a cartilage cell.

* * * * *